US008810785B2

(12) United States Patent
Lo et al.

(10) Patent No.: US 8,810,785 B2
(45) Date of Patent: Aug. 19, 2014

(54) MASK INSPECTING METHOD

(75) Inventors: Wei-Cyuan Lo, Taichung (TW); Yung-Feng Cheng, Kaohsiung (TW); Ming-Jui Chen, Tainan (TW)

(73) Assignee: United Microelectronics Corp., Science-Based Industrial Park, Hsin-Chu (TW)

( * ) Notice: Subject to any disclaimer, the term of this patent is extended or adjusted under 35 U.S.C. 154(b) by 462 days.

(21) Appl. No.: 13/218,465

(22) Filed: Aug. 26, 2011

(65) Prior Publication Data

US 2013/0050688 A1 Feb. 28, 2013

(51) Int. Cl.
*G01N 21/00* (2006.01)
*G01N 21/956* (2006.01)

(52) U.S. Cl.
CPC .... *G01N 21/956* (2013.01); *G01N 2021/95676* (2013.01)
USPC .................. 356/237.1; 356/239.1; 356/237.2

(58) Field of Classification Search
USPC ................ 356/237.1–241.6, 242.1–243.8, 356/426–431, 600–640
See application file for complete search history.

(56) References Cited

U.S. PATENT DOCUMENTS

| | | | |
|---|---|---|---|
| 4,392,120 A * | 7/1983 | Mita et al. ................ 382/199 |
| 4,805,123 A * | 2/1989 | Specht et al. .............. 382/144 |
| 5,965,306 A | 10/1999 | Mansfield |
| 6,033,811 A | 3/2000 | Lee |
| 6,084,673 A * | 7/2000 | Van Den Brink et al. .... 356/492 |
| 6,136,478 A * | 10/2000 | Usui et al. ................... 430/5 |
| 6,388,253 B1 * | 5/2002 | Su ............................. 250/310 |
| 6,395,438 B1 | 5/2002 | Bruce |
| 6,470,489 B1 | 10/2002 | Chang |
| 6,684,382 B2 | 1/2004 | Liu |
| 6,753,115 B2 | 6/2004 | Zhang |
| 6,763,514 B2 | 7/2004 | Zhang |
| 6,768,958 B2 * | 7/2004 | Ivanovic et al. ............. 702/94 |
| 6,775,815 B2 * | 8/2004 | Ki et al. ..................... 716/52 |
| 6,801,297 B2 * | 10/2004 | Nakae ........................ 355/40 |
| 6,852,453 B2 * | 2/2005 | Wu .............................. 430/5 |
| 6,961,920 B2 | 11/2005 | Zach |
| 6,969,864 B2 * | 11/2005 | Ye et al. .................. 250/559.4 |
| 7,327,436 B2 * | 2/2008 | Fukuhara et al. ........... 355/52 |
| 7,386,829 B2 | 6/2008 | Lee |
| 7,624,369 B2 | 11/2009 | Graur |
| 2004/0008879 A1 | 1/2004 | Lin |
| 2006/0066339 A1 | 3/2006 | Rajski |
| 2006/0085772 A1 | 4/2006 | Zhang |
| 2006/0161452 A1 | 7/2006 | Hess |
| 2008/0005704 A1 * | 1/2008 | Miloslavsky et al. ........ 716/2 |
| 2009/0064085 A1 * | 3/2009 | Bang ......................... 716/21 |

(Continued)

*Primary Examiner* — Tarifur Chowdhury
*Assistant Examiner* — Jarreas C Underwood
(74) *Attorney, Agent, or Firm* — Winston Hsu; Scott Margo

(57) ABSTRACT

A mask inspecting method includes the following steps. A processing parameter is defined. An incident light is decided by the processing parameter. At least a portion of the incident light is emitted to and passes through a first position and a second position of a first area of a mask, to detect a first parameter and a second parameter respectively corresponding to the first position and the second position, and then the variation of the first parameter and the second parameter is compared. Additionally, at least a portion of the incident light is emitted to and passes through a third position and a fourth position of a second area of a mask, to detect a third parameter and a fourth parameter respectively corresponding to the third position and the fourth position, and then the variation of the third parameter and the fourth parameter is also compared.

16 Claims, 4 Drawing Sheets

(56) References Cited

U.S. PATENT DOCUMENTS

| | | |
|---|---|---|
| 2009/0193385 A1 | 7/2009 | Yang |
| 2009/0278569 A1 | 11/2009 | Taoka |
| 2009/0296062 A1* | 12/2009 | Park et al. ............ 355/67 |
| 2009/0300576 A1 | 12/2009 | Huang |
| 2010/0005434 A1* | 1/2010 | Wang ............ 716/5 |
| 2010/0036644 A1* | 2/2010 | Yang et al. ............ 703/1 |
| 2010/0070944 A1 | 3/2010 | Wu |
| 2010/0086862 A1 | 4/2010 | Yang |
| 2010/0131914 A1 | 5/2010 | Wu |
| 2010/0175041 A1 | 7/2010 | Krasnoperova |
| 2011/0029939 A1 | 2/2011 | Yang |

* cited by examiner

MASK INSPECTING METHOD

BACKGROUND OF THE INVENTION

1. Field of the Invention

The present invention relates generally to a mask inspecting method, and more specifically, to a mask inspecting method that simulates optical behaviors such as a pattern image projected on a wafer from a mask using the same light with the same energy.

2. Description of the Prior Art

A conventional semiconductor process forms various semiconductor components by applying masks used for patterning wafers and semiconductor substrates. As the development of integrated circuit technologies progresses, products are becoming miniaturized, and thereby the density of circuit layouts and critical lines in semiconductor devices becomes more precise. Due to this trend, the defect tolerances of mask patterns in masks are reduced. An important issue in the field is therefore how to detect defects of mask patterns and eliminate those defects that would cause reduction in yields.

When defects are found they may be repaired, or masks may be abandoned for those defects that are impossible or not easy to be repaired. Additionally, some problems caused by defects may become worse as the defects are repaired; in other words, defect elimination requires a lot of time and money. To simplify the process, only those defects which could cause reverse effects when transferred to wafers during exposure should be eliminated. Images of a same mask pattern transferred to wafers with different processing parameters will be different, leading to different effects upon the wafers, so it is difficult to accurately simulate the transferring results of a mask in a specific parameter.

SUMMARY OF THE INVENTION

The present invention therefore provides a mask inspecting method, which can simulate the transferring images on a wafer from a mask pattern accurately to resolve the aforesaid problems of mask defects, thereby reducing processing cost and processing time.

The present invention provides a mask inspecting method including the following steps. A processing parameter is defined. An incident light is decided by the processing parameter. At least a portion of the incident light is emitted and passes through a first position and a second position of a first area of a mask, to detect a first parameter and a second parameter respectively corresponding to the first position and the second position, and then compares the variation of the first parameter and the second parameter. At least a portion of the incident light is emitted and passes through a third position and a fourth position of a second area of a mask, to detect a third parameter and a fourth parameter respectively corresponding to the third position and the fourth position, and then compares the variation of the third parameter and the fourth parameter.

The present invention provides a mask inspecting method, which applies the same light (energy) to detect defects in different positions of different areas of one mask. The mask inspecting method can determine whether these defects will reversely affect semiconductor process or sequentially formed semiconductor devices as mask patterns are transferred to wafers or semiconductor substrates.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
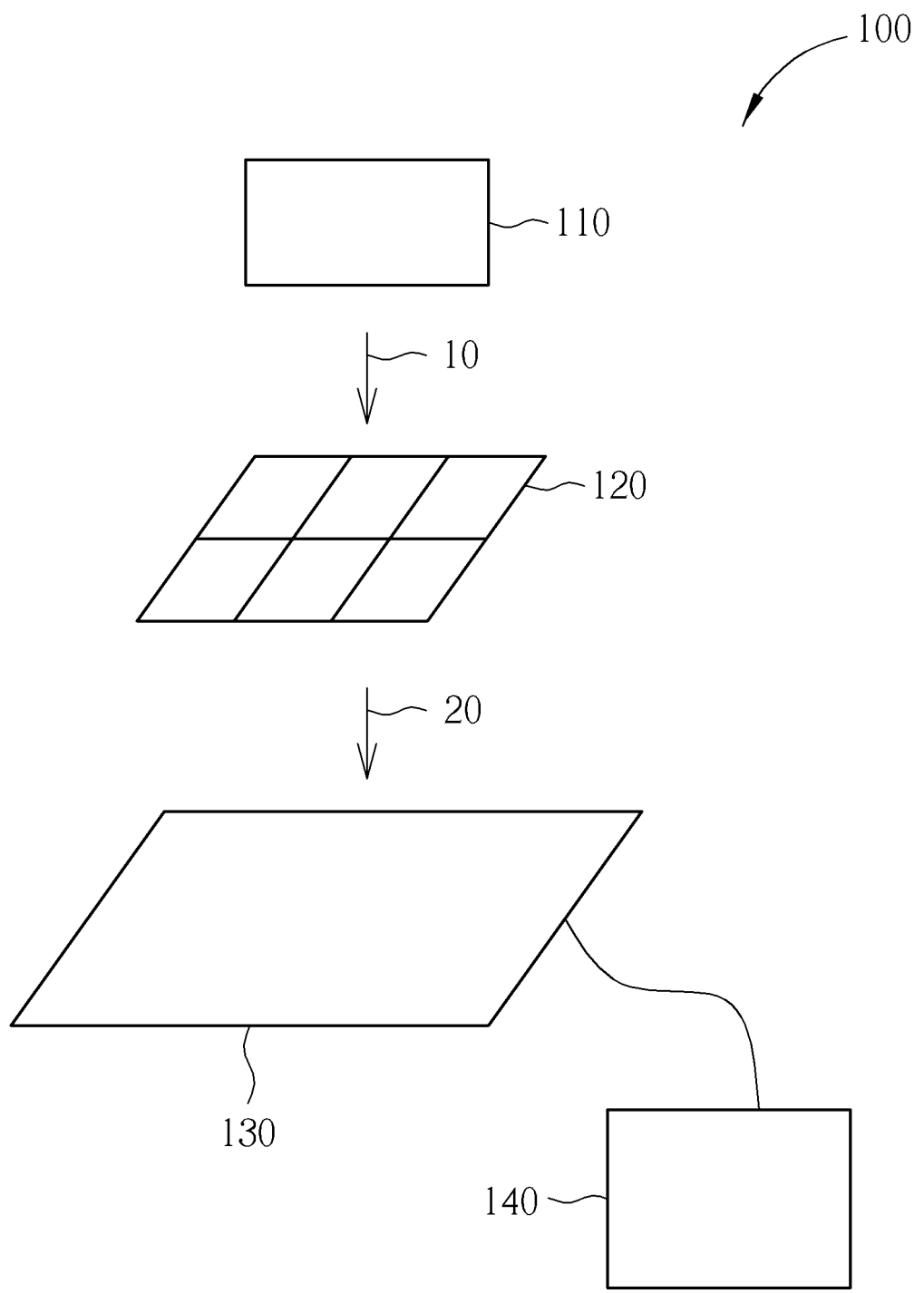
FIG. 1 schematically depicts a diagram of a mask inspecting device according to one preferred embodiment of the present invention.

FIG. 1 schematically depicts a diagram of a mask inspecting device according to one preferred embodiment of the present invention. As shown in FIG. 1, a device 100 may be an Aerial Image Measurement System (AIMS) device. The device 100 includes a light source 110, a mask 120 and a photodetector 130.

The light source 110 provides a light 10 that is emitted to the mask 120 so that the light 10 is incident on the mask 120. The light source 110 may include a mercury lamp emitting light with 365 nm wavelength, an argon fluoride excimer laser emitting light with 193 nm wavelength, or a krypton fluoride excimer laser emitting light with 248 nm wavelength etc, for providing the light 10 with needed energy or wave band. The light 10 may be an ultraviolet (UV) light, a deep ultraviolet (DUV) light, an X-ray, a light with 365 nm wavelength (I-line), a light with 248 nm wavelength, or a light with 193 nm wavelength. The light 10 is chosen depending upon the properties of the mask 120 and exposure process environment being simulated.

At least a portion of the light 10 emitted to the mask 120 passes through the mask 120 and transforms to a light 20. The mask 120 has mask patterns thereon, and the mask patterns are designed according to integrated circuit patterns which need to be formed on a semiconductor substrate. In one embodiment, the mask may include an absorbing layer, a metal film, an inorganic film, a binary intensity mask (BIM), a phase-shift mask (PSM) or an optical proximity correction (OPC) mask etc. Thus, the light 20 and light 10 may have different or the same phase, amplitude, direction, wavelength etc. depending upon the properties of the mask 120.

The light 20 is emitted to the photodetector 130 disposed in the light path of the light 20; that is, in the light path of the light 10 after it passes through the mask 120. The light 20 is then received by the photodetector 130 for detecting images or parameters corresponding to mask patterns of the mask 120, wherein the photodetector 130 may be a light reaction membrane, a particle sensor, a CMOS image sensor, or a coupled device image sensor etc.

The device 100 may further include a processor 140 that connects to the photodetector 130, receives and analyzes the detecting data of the photodetector 130, and then determines whether defects of the mask pattern of the mask 120 need to be repaired or not.

Figure 2:
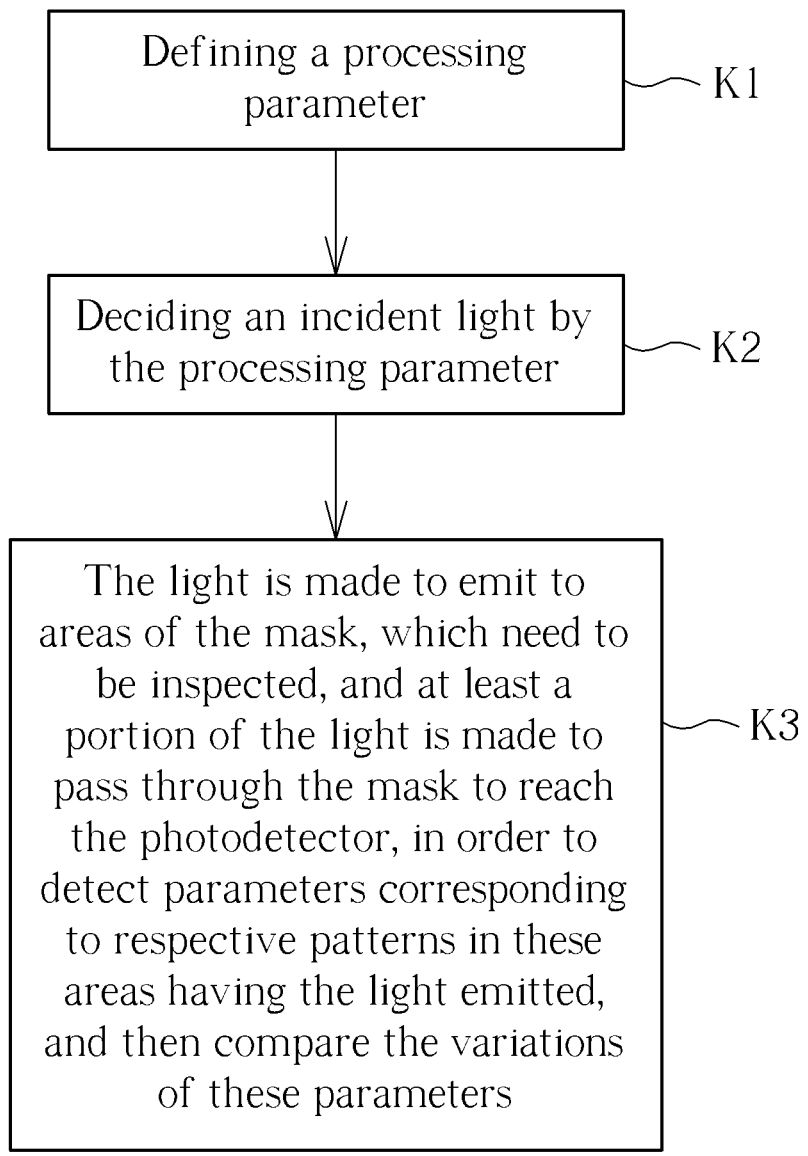
FIG. 2 schematically depicts a flow chart of a mask inspecting method according to one preferred embodiment of the present invention.

The present invention provides a mask inspecting method applying the aforesaid device 100 to inspect defects of the mask patterns of the mask 120. FIG. 2 schematically depicts a flow chart of a mask inspecting method according to one preferred embodiment of the present invention. As shown in FIG. 2, a processing parameter P is defined according to the properties of the mask 120 and the setups of the mask 120 set during manufacturing (Step K1). For example, a processing parameter P may be a critical dimension of a test pattern on the mask 120, such as a CD-bar, but it is not limited thereto, wherein any product or layer should have a CD-bar (often disposed on a scribe lane); the minimum rule for the product or layer is illustrated. The energy of the incident light 10 can be decided by the processing parameter P (Step K2). In this embodiment, the energy threshold corresponding to the critical dimension is used as the energy of the light 10. After the energy of the light 10 is decided, the light 10 is made to emit to areas of the mask 120 which need to be inspected, and at least a portion of the light 10 is made to pass through the mask 120 to reach the photodetector 130, in order to detect parameters corresponding to respective patterns in these areas having the light 10 emitted, and then compare the variations of these parameters (Step K3).

Figure 3:
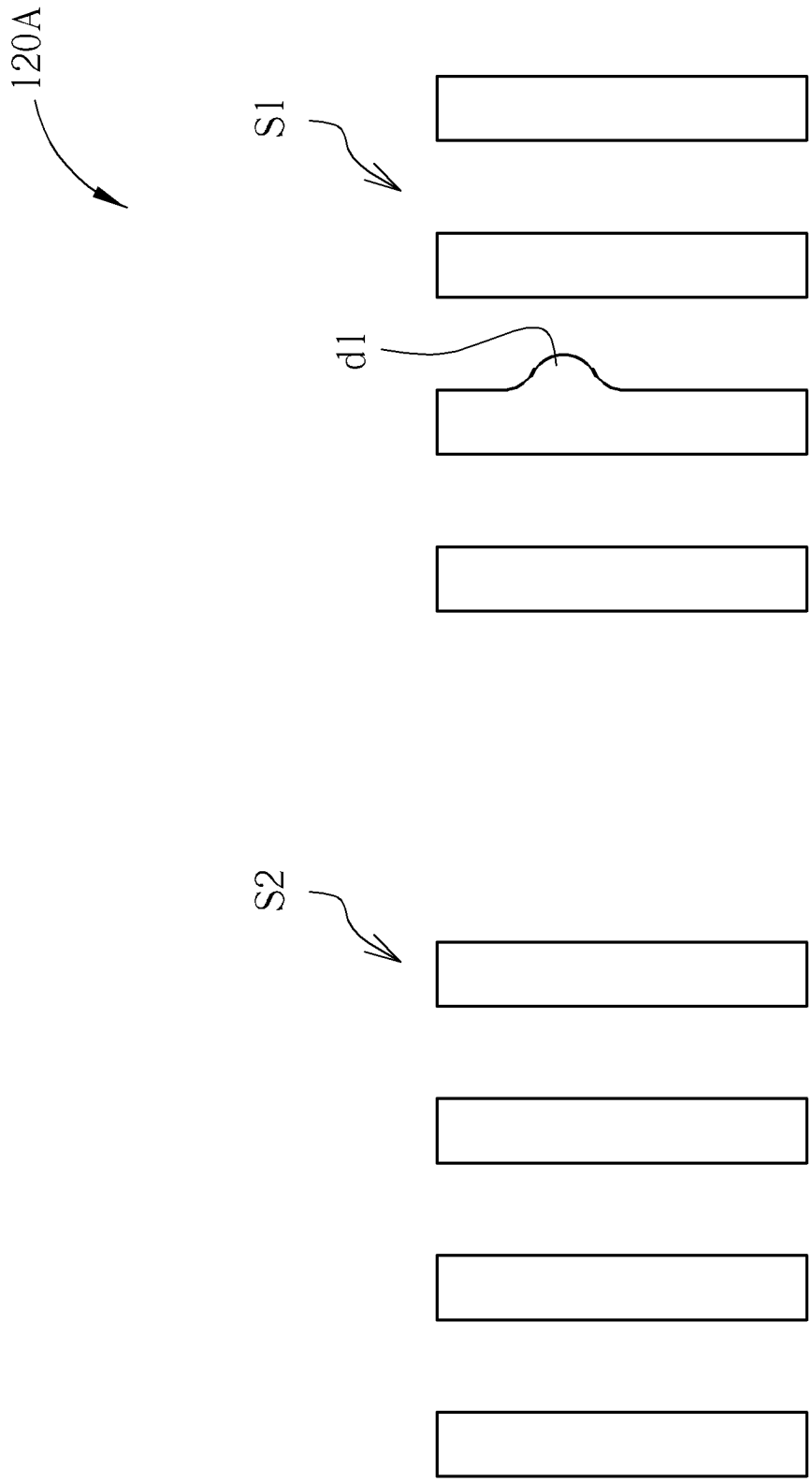
FIG. 3 schematically depicts a diagram of a dense pattern area of a mask according to one preferred embodiment of the present invention.
Figure 4:
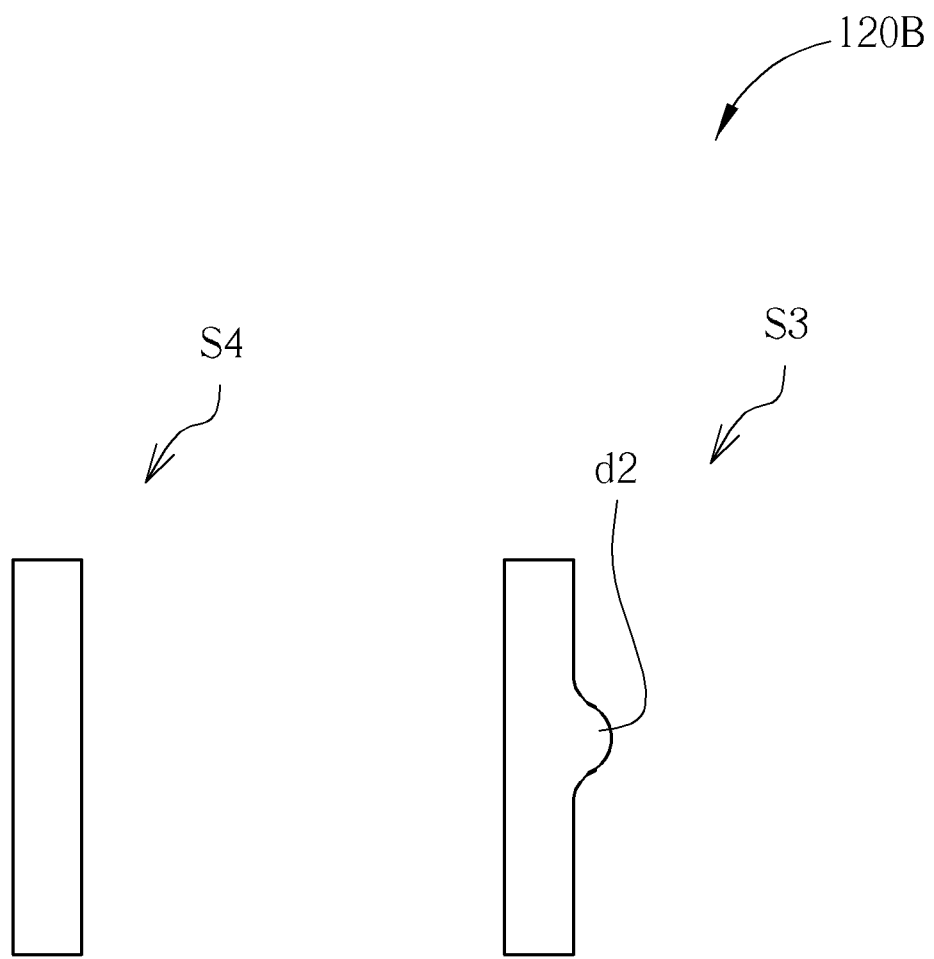
FIG. 4 schematically depicts a diagram of an isolated pattern area of a mask according to one preferred embodiment of the present invention.

FIG. 3 schematically depicts a diagram of a dense pattern area of a mask according to one preferred embodiment of the present invention. FIG. 4 schematically depicts a diagram of an isolated pattern area of a mask according to one preferred embodiment of the present invention. As shown in FIG. 3, when a defect d1 (shown on the right-hand side of FIG. 3) included in a first position S1 of a first area 120A of the mask 120 is found, the light 10 is made to emit to the first position S1 to detect and get a corresponding first parameter P1. Thereafter, the light 10 is made to emit to the second position S2, which is a non-defect area (as shown on the left-hand side of FIG. 3), to detect and get a corresponding second parameter P2. Then, the variation of the first parameter P1 and the second parameter P2 is compared. When the variation of the first parameter P1 and the second parameter P2 is larger than a predetermined variation tolerance, this means the defect d1 needs to be repaired. When the variation of the first parameter P1 and the second parameter P2 is smaller than a predetermined variation tolerance, this means the defect d1 in a predetermined processing environment will not cause reverse effects to processes. Therefore, the defect d1 can be ignored.

Areas with different optical properties of the mask 120 are inspected by the same incident light 10. As shown in FIG. 4, when a defect d2 included in a third position S3 of a second area 120B of the mask 120 is found (as shown on the right-hand side of FIG. 4), the same light 10 is made to emit to the third position S3 to detect and get a corresponding third parameter P3. Then, the same light 10 is made to emit to the fourth position S4, which includes a non-defect area (as shown on the left-hand side of FIG. 4) to detect and get a corresponding fourth parameter P4. Thereafter, the variation of the third parameter P3 and the fourth parameter P4 is compared. When the variation of the third parameter P3 and the fourth parameter P4 is larger than a predetermined variation tolerance, this means the defect d2 needs to be repaired. When the variation of the third parameter P3 and the forth parameter P4 is smaller than a predetermined variation tolerance, this means the defect d2 in a predetermined processing environment will not cause reverse effects to processes. Therefore, the defect d2 can be ignored.

The first parameter P1, the second parameter P2, the third parameter P3 and the fourth parameter P4 in this embodiment are the critical dimensions corresponding to various positions of mask patterns, but are not limited thereto. Additionally, the second area 120B of this embodiment has different optical properties from the first area 120A, but it is not limited thereto. For instance, the first area 120A and the second area 120B may have different pattern densities. In this embodiment, the first area 120A as shown in FIG. 3 is a dense pattern area, and the second area 120B is an isolated pattern area. The isolated pattern area has a largest separation between adjacent features and the dense pattern area has a smallest separation between adjacent features. In other words, the dense pattern area and the isolated pattern area respectively represent the highest density area and the lowest density area of a wafer, therefore the critical dimension of every areas in a wafer is in the range between the dense pattern area and the isolated pattern area.

The emitting order of the light 10 can be changed. For example, the second position S2 may be emitted first and then the first position S1 is emitted, or the fourth position S4 may be emitted first and then the third position S3 is emitted. Furthermore, the light 10 is not restricted to emit to the first position S1 and the second position S2 of the first area 120A of the mask 120. It can also emit to another position or other positions (a single position or multiple positions) in the first area 120A, to respectively detect parameters corresponding these positions, and then compare the variations of these parameters, the first parameter P1 or the second parameter P2; the same applies to the second area 120B. The light 10 of the present invention is not restricted to emit to the first area 120A and the second area 120B of the mask 120; it may also emit to multiple positions in other areas of the mask 120 and is not limited thereto.

It should be noted that the present invention uses the same light 10, which has the same energy, to emit to different areas of the mask 120 such as the first area 120A and the second area 120B, to respectively detect defects indifferent areas. The reason is that only single-energy light is used to emit to a mask in modern processes for exposing the same wafer or the same semiconductor substrate. Therefore, the present invention decides the light 10 (energy) according to the properties of the mask 120 and the processing parameters first, and then fixes the light 10 (energy) to emit to various areas on the mask 120, and particularly to emit to various areas with different optical properties, such as a dense pattern area, or an isolated pattern area etc. In doing this, the simulation result of the present invention can be closer to the exposing result of an exposure process. Defects such as defects d1 and d2 in the mask 120 can be determined accurately by deciding whether these defects will affect images transferring to wafers or semiconductor substrates or not, and therefore determining the usefulness of the masks.

Above all, the present invention provides a mask inspecting method, which applies the same light (energy) to detect defects in different positions of different areas of one mask, for processing these defects accurately. The mask inspecting method can determine whether these defects will reversely affect the images transferring to wafers or semiconductor substrate or not. That is, due to the same light being used while an exposure process is performed, the present invention only needs to use one light (energy) to inspect one mask in order to simulate the actual exposing result accurately. In this way, repairs performed on defects which do not cause reverse effects due to simulation errors can be submitted, and the likelihood of defects causing reverse effects while exposure processes are performed will be reduced. The present invention can improve processing yields and also reduce processing costs.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A mask inspecting method, comprising:
defining a processing parameter;
deciding an incident light by the processing parameter;
making at least a portion of the incident light pass through a first position and a second position of a first area of a mask, to detect a first parameter and a second parameter respectively corresponding to the first position and the second position, and then comparing the variation of the first parameter and the second parameter; and
making at least a portion of the incident light pass through a third position and a fourth position of a second area of a mask, to detect a third parameter and a fourth parameter respectively corresponding to the third position and the fourth position, and then comparing the variation of the third parameter and the fourth parameter, wherein the first area and the second area have different optical properties.

2. The mask inspecting method according to claim 1, wherein the processing parameter comprises a critical dimension.

3. The mask inspecting method according to claim 2, wherein the processing parameter comprises a critical dimension of a CD-bar.

4. The mask inspecting method according to claim 1, wherein the step of deciding the incident light by the processing parameter comprises deciding the incident energy of the incident light.

5. The mask inspecting method according to claim 1, wherein the first area and the second area have different optical properties.

6. The mask inspecting method according to claim 5, wherein the first area and the second area have different pattern densities.

7. The mask inspecting method according to claim 6, wherein the first area comprises a dense pattern area and the second area comprise an isolated pattern area.

8. The mask inspecting method according to claim 1, wherein the first position and the third position comprise at least a defect.

9. The mask inspecting method according to claim 1, wherein the second position and the fourth position have no defect.

10. The mask inspecting method according to claim 1, wherein the first parameter, the second parameter, the third parameter and the fourth parameter comprise a critical dimension.

11. The mask inspecting method according to claim 1, further comprising:
making at least a portion of the incident light pass through other positions of the first area, to detect other parameters corresponding to the other positions, and then comparing the variations of other parameters, the first parameter and the second parameter.

12. The mask inspecting method according to claim 1, further comprising:
making at least a portion of the incident light pass through multiple positions of other areas of the mask to detect multiple parameters corresponding to the multiple positions and comparing the variations of the multiple parameters.

13. The mask inspecting method according to claim 1, wherein the incident light is emitted by a light source and the light source comprises a mercury lamp with 365 nm, an argon fluoride excimer laser with 193 nm, or a krypton fluoride excimer laser with 248 nm.

14. The mask inspecting method according to claim 1, wherein the mask comprises an absorbing layer, a metal film, an inorganic film, a binary intensity mask (BIM), a phase-shift mask (PSM) or an optical proximity correction (OPC) mask.

15. The mask inspecting method according to claim 1, further comprising:
providing a photodetector disposed on the light path of the incident light after it passes through the mask to detect the first parameter, the second parameter, the third parameter and the fourth parameter.

16. The mask inspecting method according to claim 15, further comprising:
providing a processor, connected to the photodetector, for receiving the detecting data of the photodetector to compare the variation of the first parameter and the second parameter and the variation of the third parameter and the fourth parameter.

* * * * *